United States Patent [19]

Römhild et al.

[11] Patent Number: 4,979,899
[45] Date of Patent: Dec. 25, 1990

[54] SCALER FOR CLEANING TEETH

[75] Inventors: Ludwig Römhild, Am Kugelfeld 3, Berchtesgaden, Fed. Rep. of Germany; Erwin Hartmann, Möriken, Switzerland

[73] Assignees: Ludwig Römhild, Berchtesgaden, Fed. Rep. of Germany; Peter Reinhard, Spreitenbach, Switzerland

[21] Appl. No.: 196,436

[22] Filed: May 20, 1988

[30] Foreign Application Priority Data

Jun. 3, 1987 [CH] Switzerland .......................... 2107/87

[51] Int. Cl.$^5$ .............................................. A61C 1/07
[52] U.S. Cl. .................... 433/121; 433/122; 433/118
[58] Field of Search ............... 433/122, 123, 165, 166, 433/118, 121, 125

[56]     References Cited
U.S. PATENT DOCUMENTS

| 2,924,012 | 2/1960 | Ellis | 433/123 |
| 3,967,380 | 7/1976 | Malata et al. | 433/122 |
| 4,175,324 | 11/1979 | Arai | 433/122 |
| 4,341,519 | 7/1982 | Kuhn et al. | 433/121 X |
| 4,781,588 | 11/1988 | Granier | 433/122 X |

FOREIGN PATENT DOCUMENTS

| 3320211 | 12/1984 | Fed. Rep. of Germany | 433/118 |
| 3438462 | 1/1986 | Fed. Rep. of Germany | 433/125 |

Primary Examiner—Robert P. Swiatek
Assistant Examiner—Nicholas D. Lucchesi
Attorney, Agent, or Firm—Helfgott & Karas

[57]     ABSTRACT

The scaler includes a housing which is an angle piece and includes a grip housing and an instrument housing positioned at an angle to the grip housing. A scraper is inserted in a bearing sleeve mounted in bearings in the instrument housing and can be moved into different angular positions relative to the circumference of the bearing sleeve and can be fixed by rotating a coupling ring. A drive shaft is mounted in the grip housing. The drive shaft at its end face is provided with an eccentrically positioned driving pin and a coaxial bearing pin. An eccentric member is pivotable within an angular range on the bearing pin. This range is determined by the size of a recess formed in the eccentric member. A spring-loaded rocker cooperates with the eccentric member to perform a rapid jerky movement of the scraper relative to the instrument housing when the eccentric surface formed in the eccentric member faces the rocker.

14 Claims, 2 Drawing Sheets

SCALER FOR CLEANING TEETH

BACKGROUND OF THE INVENTION

The invention relates to a scaler for cleaning teeth, in which the instrument is constituted by a scraping insert having a cutting edge and which is mounted in a handle. The scraper insert is driven by means of a drive shaft by drive means, whilst producing a relatively rapid sudden or jerky outward movement towards the handle and a relatively slow return movement away from the handle.

The scaler is a well-known instrument used by the dentist in treating teeth and is used for cleaning the latter, and more especially for the removal of coatings of tartar, concretions and root cement on the parts located below the gums. In a known scaler (EP-A-O 221 460) drive means with a rotary drive shaft and transmission means are provided in the handle, by means of which a scraper body mounted in the handle performs a slow movement of the scraper in the direction away from the handle and which slow movement is followed by a sudden return movement towards the handle. The impact rod performing these movements is coupled to an impact body for mass equilibrium reasons and said impact body performs a movement opposite to that of the impact rod. With this scaler the instrument is located quietly in the operator's hand and therefore an impairing of the sudden return movement to the scraper is avoided, so that it is possible to work in a completely satisfactory manner with this known scaler. However, it is disadvantageous that the scaler is constructed as a rod-like instrument, i.e. the handle and scraper are aligned. It is impossible or only possible with considerable effort when using such an instrument to treat certain teeth, particularly parts of teeth in the pharyngeal area.

SUMMARY OF THE INVENTION

It is an object of the present invention to further develop a scaler of the aforementioned type so that it can be easily and effortlessly handled even when treating the tooth parts which are difficult to reach.

According to the invention this object is attained in that the handle is constructed as an angle piece with a grip housing arranged on the drive side and with an instrument housing arranged at an angle to the grip housing.

Admittedly dentistry working appliances with rotary and reciprocating instruments are known (DE-OS 3 320 211), but with these appliances it is not possible to perform the typical jerky movement of the scraper towards the handle and the slow movement away from the handle during treatment with the scaler.

An embodiment of the invention is described in greater detail hereinafter relative to the drawings.

BRIEF DESCRIPTION OF THE DRAWING

FIGS. 4a and 4b show a front view of the drive parts positioned on the drive shaft of the scaler, wherein FIG. 4a shows the eccentric member before and FIG. 4b shows this member after tilting over.

DETAILED DESCRIPTION OF THE PREFERRED EMBODIMENT

Figure 1:
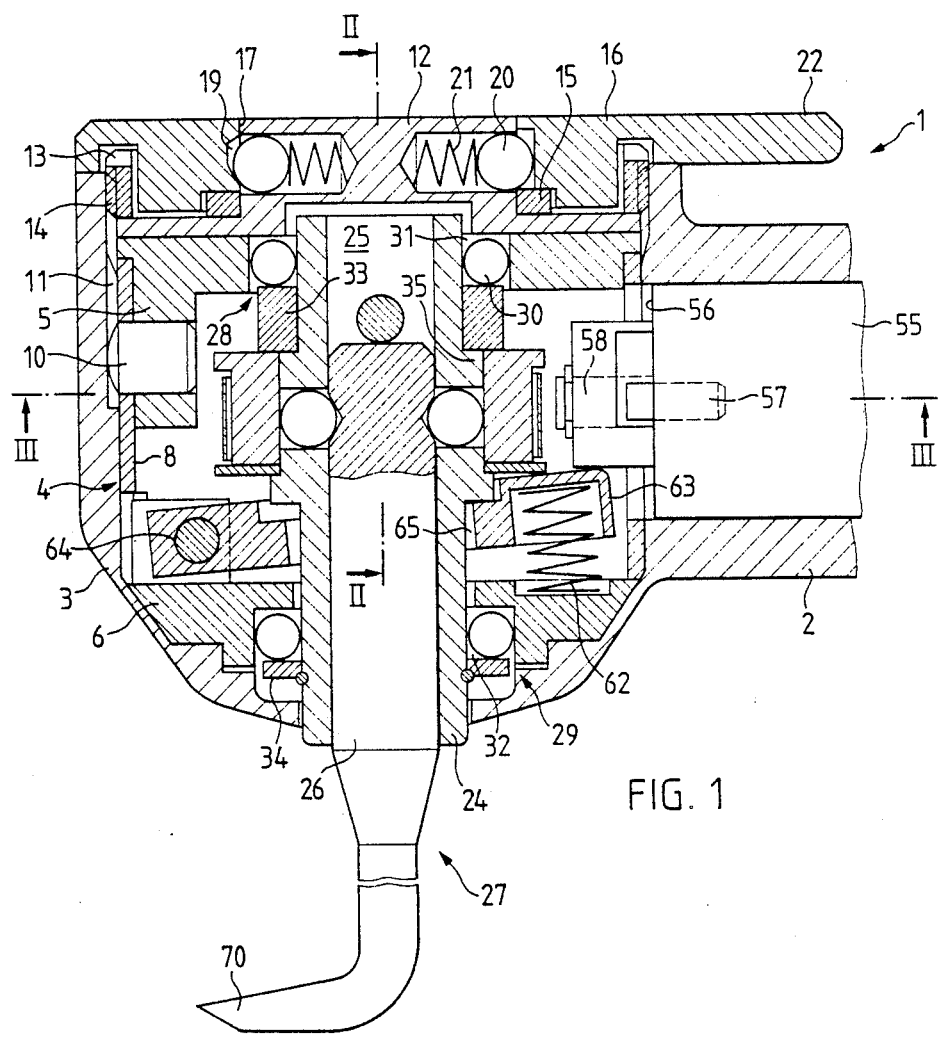
FIG. 1 is a longitudinal section through a scaler, whose scraper is mounted in an instrument housing at an angle to the grip housing.

The scaler 1 shown in FIG. 1 has a housing constructed as an angle piece and which comprises an only partly shown grip housing 2 and an instrument housing 3. The grip housing 2 can be coupled in a known manner to the motor or to the flexible shaft of the main drive of a dental appliance. The scaler according to FIG. 1 consequently does not require its own drive, as is the case with the aforementioned known scaler.

In the instrument housing 3 is placed an inner casing 4, which comprises an upper bearing web 5, a lower bearing web 6 and an intermediate thrust ring 8. A guide bolt 10 connects the upper bearing web 5 and the thrust ring 8 to each other and projects into a guide groove 11 made in the inner wall of the instrument housing. Thus, the inner casing 4 is positioned with respect to the instrument housing 3.

On the upper bearing web 5 is placed a cover 12 which, together with the inner casing 4, is secured by a ring nut 13 screwed into an internal thread 14 in the inner wall of the instrument housing 3. A ball holding ring 15 is placed in cover 12.

Cover 12 is surrounded by an operating ring 16 having a bore 17, in which is formed a radial groove, in which locking members 20, e.g. balls, loaded by a spring 21 for the purpose of mounting the operating ring 16, are inserted. For the purpose of positioning the operating ring 16 two positioning recesses 19 (only one visible in FIG. 1) are provided for engagement of one of the locking members 20. Operating ring 16 is provided with the adjusting means used for its adjustment, e.g. a lever 22 or a knurled head (not shown). Within the inner casing 4 is mounted a bearing sleeve 24, which has a bore 25 for receiving a shaft 26 of a scraper 27. Bearing sleeve 24 is axially displaceably guided at its ends in bearings 28, 29. The latter are constructed as antifriction bearings with antifriction balls 30, which are located in recesses 31,32 of the inner casing 4, the recess 31 of the upper bearing 28 being defined by the cover 12 and by a thrust ring 33 and the recess 32 of the lower bearing 29 by the lower bearing web 6 and a thrust ring 14 supported on bearing sleeve 24. The latter has a part 35 between bearings 28,29 having a greater wall thickness.

Figure 2:
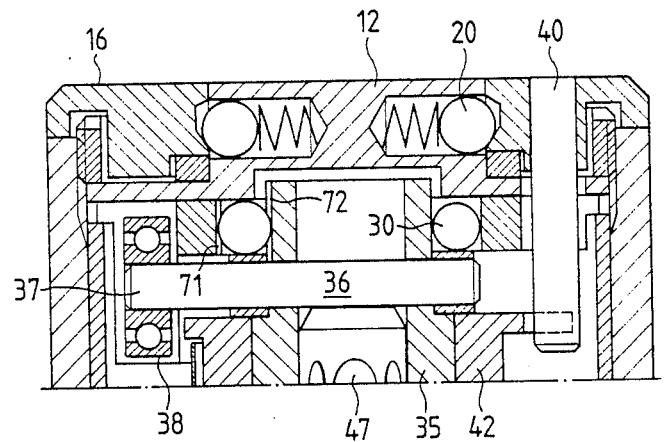
FIG. 2 is a section along line II—II of the scaler shown in FIG. 1.

FIG. 2 shows the upper part of the instrument housing 3. A locking pin 36 extends diagonally through the bearing sleeve 24 over the greater wall thickness part 35 of said sleeve 24. At one end 37 the locking pin carries an antifriction bearing 38, which is guided in a slit 39 of the upper bearing web 5. Rotation of bearing sleeve 24 is made impossible by the locking pin 36 guided in slit 39. This is important, because the scaler exerts lateral forces under which the bearing sleeve 24 must not give way.

Figure 3:
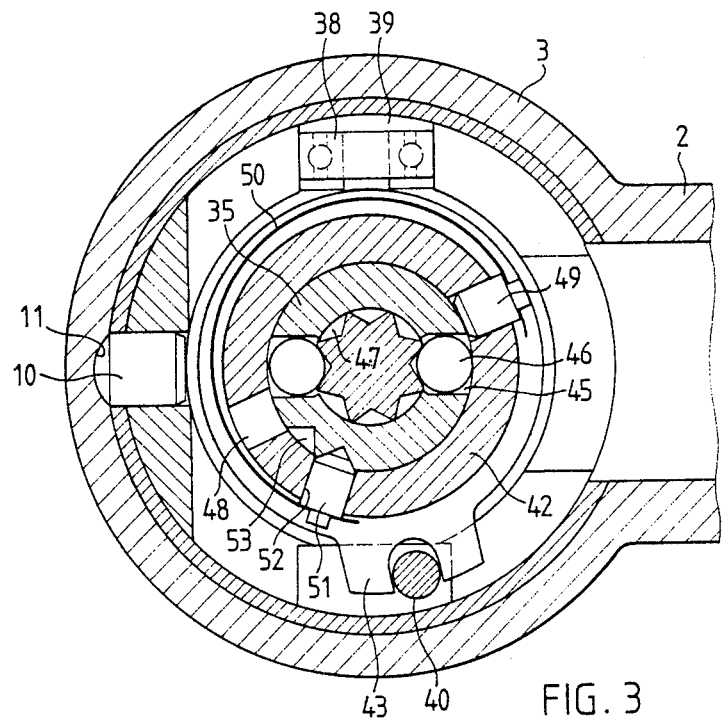
FIG. 3 is a section along line III—III of the scaler shown in FIG. 1.

In FIG. 2 there is also a driving pin 40 fixed in operating ring 16 and projecting into the larger diameter part 35 of bearing sleeve 24 which is surrounded by a coupling ring 42 provided on its outer circumference with an operating or shift fork 43 into which projects the driving pin 40, as shown in FIG. 3. The function of coupling ring 42 can be best explained with reference to FIG. 3.

Part 35 of bearing sleeve 24 contains two diametrically opposing bores 45 in which are guided coupling bodies 46, e.g. balls which, in the position shown in FIG. 3, project into depressions 47 located in the outer circumference of shaft 26 of scraper 27 and therefore couple the scraper body with the bearing sleeve 24. For uncoupling, i.e. during changing or rotating the scraper into a new position, the coupling ring 42 is turned until two diametrically positioned bores 48 formed therein are aligned with respective bores 45 of bearing sleeve 24. A stud 49 is held by an annular spring 50 in one bore 48 of coupling ring 42. The other end of the annular spring 50 acts on a positioning bolt 51, which is positioned in a bore 52 of coupling ring 42 and projects into depressions 53 located in the outer circumference of bearing sleeve 24.

In the position shown in FIG. 3 the coupling bodies 46 are locked in depressions 47 of shaft 26. If the coupling ring 42 is now rotated clockwise until bores 48 are aligned with bores 45, the coupling bodies 46 can withdraw into the bores 48, so that scraper 27 can be replaced, removed or turned into a new position. Positioning bolt 51 is locked in the adjacent recess 53 in the uncoupled position. It is consequently possible to maintain the coupling position of coupling ring 42. The displacement of the coupling ring 42 takes place by rotating the operating ring 16, so that the driving pin 40 rotates the operating fork 43 and therefore the coupling ring 42 into the desired position.

Figure 4A:
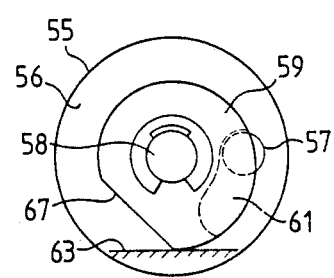

The typical movement sequence for the scaler is best described with reference to FIGS. 1 and 4a, 4b. A drive shaft 55 is mounted in the rotary manner in grip housing 2 and is provided on its end at the transition to the end face 56 with a driving pin 57. Driving pin 57 is arranged eccentrically to the axis of drive shaft 55. Coaxially with respect to the drive shaft 55 is arranged a bearing pin 58 on which an eccentric member 59 is rotatably mounted. The eccentric member 59 is secured by a circlip 60. Eccentric member 59 has a recess 61 positioned against the end face 56 of drive shaft 55 and which extends over approximately 40–70° of the circumference. The driving pin 57 projects into recess 61.

The eccentric member 59 is connected to a rocker 63 loaded by a spring 62 and which is pivotable about a pivot pin 64. The rocker 63 extends substantially over the inner area formed by thrust ring 8 and has a passage 65 for the bearing sleeve 24, so that spring 62 and pivot pin 64 are arranged on the opposite sides of bearing sleeve 24. With the aid of the eccentric member 59 freely movable within the range of recess 61, the desired jerky scaler movement relative to the instrument housing 3 is obtained in the following manner.

Figure 4B:
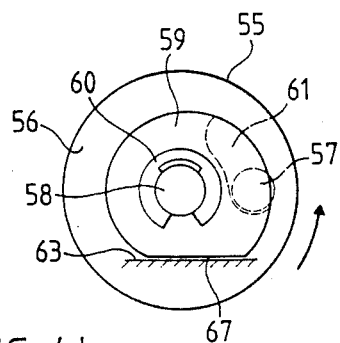

A counterclockwise arrow in FIG. 4b indicates the movement direction of drive shaft 55. The driving pin 57 is located at the end of recess 61 shown in FIG. 4a and carries with it the eccentric member 59. When the lower edge of eccentric member 59 has reached the position shown in FIG. 4a, the eccentric member tilts over into the position shown in FIG. 4b, so that the spring-loaded rocker 63 engages in a jerky movement of scraper 27. The driving pin 57 cannot follow this jerky movement of eccentric member 59 and remains in the position shown in FIG. 4b. Only on reassuming its position in recess 61 according to FIG. 4a, does it again take the eccentric member 59 with it. This jerky advance of the eccentric member 59 is repeated during each rotation of drive shaft 55.

It is pointed out that the jerky movement of scraper 27 only takes place if its cutting edge 70 is engaged on a tooth and the bearing sleeve is moved away from the instrument housing 3. If cutting edge 70 does not engage on a tooth, then the bearing sleeve 24 is moved against cover 12 and there is no reciprocating movement of scraper 27.

A number of variants for the scaler construction are possible within the inventive concept. Thus, the housing sleeve 24 can be mounted in sliding bearings instead of antifriction bearings 28,29, so that possibly a somewhat greater friction can occur. As shown in FIG. 2, in place of the locking pin 36 for preventing a rotation of part 35, one of the balls 30 can be made somewhat larger and projects into slots 71,72 made in the inner casing 4 and the bearing sleeve 24.

As a result of the described construction of the instrument housing 3, it is ensured that the jerky movement of the cutting edge towards the instrument housing 3 required for the use of a scaler is achieved in a relatively simple manner by the eccentric member 59 freely movable within a certain angular range.

We claim:

1. A scaler for cleaning teeth, comprising a handle having a grip housing and an instrument housing; an instrument located in said instrument housing; a scraper mounted in said instrument; drive means in said grip housing for driving said scraper with a relatively rapid jerky movement toward said handle and a relatively slow return movement away from said handle, said handle being constructed as an angle piece with said instrument housing arranged at an angle to said grip housing; a bearing sleeve receiving said scraper and being axially displaceably mounted in said instrument housing; and coupling means operatively interconnected between said drive means and said bearing sleeve for driving said scraper, said bearing sleeve having ends mounted in bearings, said coupling means being positioned between said bearings, said drive means comprising a drive shaft housing thereof, an eccentrically fixed driving pin on an inner end face and a bearing pin coaxial with said drive shaft, the bearing pin carrying a rotary eccentric member having an eccentric surface and a circumferential recess receiving said driving pin.

2. Scaler according to claim 1, wherein the bearing sleeve is mounted in an inner casing, which is formed by an upper bearing web, a lower bearing web and at least one thrust ring located between the bearing webs.

3. Scaler according to claim 1, wherein the instrument housing is terminated by a cover facing the scraper.

4. Scaler according to claim 3, wherein the instrument housing has inner casing and the cover is fixed against the inner casing by an annular nut, which is screwed into an internal thread arranged on the inner wall of the instrument housing.

5. Scaler according to claim 3, wherein the cover has an operating ring having at least two position recesses and spring-mounted radially extending locking members, one of which can be locked in one of said two positioning recesses of said operating ring.

6. Scaler according to claim 1, wherein securing means are provided for holding the bearing sleeve in non-rotary, but axially displaceable manner in the instrument housing.

7. A scaler according to claim 1, wherein a spring-loaded rocker is pivotally mounted in said lower bearing web adjacent said eccentric surface of said eccentric member, and said rocker is arranged to act upon said bearing sleeve to provide said jerky motion of said scraper upon rotation of said eccentric member.

8. A scaler according to claim 1, wherein said scraper has a cutting tip and a cylindrical shaft having circumferential depressions therein to enable said cutting tip to be fixed in different angular positions with respect to said grip housing.

9. The scaler according to claim 1, wherein said drive shaft extends parallel to the axis of said grip housing, said eccentric member being rotatably coupled to said drive shaft, and wherein said drive means further includes a spring-loaded rocker member located between said eccentric member and said bearing sleeve for driving said scraper with a rapid jerky toward said handle and slower motion away from said handle during each rotation of said drive shaft.

10. The scaler of claim 1, wherein the eccentric member is rotatably coupled to said drive shaft by said driving pin.

11. A scaler for cleaning teeth, comprising a handle having a grip housing and an instrument housing; an instrument located in said instrument housing; a scraper mounted in said instrument; drive means in said grip housing for driving said scraper with a relatively rapid jerky movement toward said handle and a relatively slow return movement away from said handle, said handle being constructed as an angle piece with said instrument housing arranged at an angle to said grip housing; a bearing sleeve receiving said scraper and being axially displaceably mounted in said instrument housing; and coupling means operatively interconnected between said drive means and said bearing sleeve for driving said scraper, said bearing sleeve having ends mounted in bearings, said coupling means being positioned between said bearings, wherein the bearing sleeve has radially displaced positioning depressions and radial bores with coupling bodies displaceable therein, and said coupling means comprises a coupling ring having radial bores, a stud and an annular ring for moving said coupling ring to an uncoupling position wherein said radial bores of said bearing sleeve and said coupling ring are aligned, and a spring loaded positioning bolt for engagement with said depressions to define the coupling and uncoupling positions.

12. Scaler according to claim 11, wherein said coupling means also has a driving pin and the coupling ring has an operating fork through which it can be pivoted by said driving pin into the uncoupling and coupling position.

13. Scaler according to claim 12, wherein the instrument housing has a cover and the driving pin is fixed in a rotary operating ring guided on said cover.

14. A scaler for cleaning teeth, comprising a handle having a grip housing and an instrument housing; an instrument located in said instrument housing; a scraper mounted in said instrument; drive means in said grip housing for driving said scraper with a relatively rapid jerky movement toward said handle and a relatively slow return movement away from said handle, said handle being constructed as an angle piece with said instrument housing arranged at an angle to said grip housing; a bearing sleeve receiving said scraper and being axially displaceably mounted in said instrument housing; and coupling means operatively interconnected between said drive means and said bearing sleeve for driving said scraper, said bearing sleeve having ends mounted in bearings, said coupling means being positioned between said bearings, said bearing sleeve being mounted in an inner casing, which is formed by an upper bearing web, a lower bearing web and thrust rings located between the bearing webs, wherein the ends of said bearing sleeve are mounted in antifriction bearings formed by antifriction balls, which are arranged in recesses of the upper and lower bearing webs and are defined by said thrust rings arranged on bearing sleeve.

* * * * *